United States Patent [19]

Novy, Jr. et al.

[11] Patent Number: 5,858,724
[45] Date of Patent: Jan. 12, 1999

[54] RECOMBINANT RABBIT TISSUE FACTOR

[75] Inventors: Robert E. Novy, Jr., Verona; Michael J. Domanico, Madison; Keith W. Yaeger, Madison; Warren Kroeker, Madison, all of Wis.

[73] Assignee: Pel-Freez, Rogers, Ark.

[21] Appl. No.: 683,007

[22] Filed: Jul. 16, 1996

[51] Int. Cl.$^6$ .................. C07K 14/745; C07K 14/245; C12N 15/12; C12N 5/10
[52] U.S. Cl. .................. 435/69.6; 435/69.7; 435/252.33; 530/381; 530/415; 536/23.1; 536/23.5; 536/23.7; 536/24.1
[58] Field of Search .................. 435/69.7, 252.33, 435/69.6, 320.1; 530/381, 415, 323, 827; 536/23.5, 23.7, 24.1, 23.1

[56] References Cited

U.S. PATENT DOCUMENTS

| | | | |
|---|---|---|---|
| 4,877,830 | 10/1989 | Dobeli et al. | 525/54.3 |
| 5,017,556 | 5/1991 | O'Brien et al. | 514/2 |
| 5,110,730 | 5/1992 | Edgington et al. | 435/69.6 |
| 5,270,181 | 12/1993 | McCoy et al. | 435/69.7 |
| 5,298,599 | 3/1994 | Rezaie et al. | 530/350 |
| 5,317,695 | 5/1994 | Brown | 424/450 |
| 5,643,757 | 7/1997 | Malik et al. | 435/69.7 |
| 5,646,016 | 7/1997 | McCoy et al. | 435/69.7 |

FOREIGN PATENT DOCUMENTS

93/07492  4/1992  WIPO .

OTHER PUBLICATIONS

Fiore, et al., "The Biochemical Basis for the Apparent Defect of Soluble Mutant Tissue Factor in Enhancing the Proteolytic Activities of Factor VIIa*," *The Journal of Biological Chemistry*, 269:143–149 (1994).

Fisher, et al., "Cloning and Expression of Human Tissue Factor cDNA," *Thrombosis Research*, 48:89–99 (1987).

Morrissey, et al., "Quantitation of Activated Factor VII Levels in Plasma Using A Tissue Factor Mutant Selectively Deficient in Promoting Factor VII Activation," *Blood*, 81:734–744 (1993).

Pawashe, et al., "Molecular Cloning, Characterization and Expression of cDNA for Rabbit Brain Tissue Factor," *Thrombosis and Haemostasis*, 66:315–320 (1991).

Spicer, et al., "Isolation of cDNA clones coding for human tissue factor: Primary structure of the protein and cDNA," *Proc. Natl. Acad. Sci. USA*, 84:5148–5152 (1987).

Proba et al., Functional antibody single–chain fragments from the cytoplasm of *Escherichia coli* : influence of thioredoxin reductase (TrxB), Gene, 159: 203–207, Oct. 1995.

LaVallie et al., A thioredoxin gene fusion expression system that circumvents inclusion body formation in the *E. coli* cytoplasm, Bio/Technology, 11: 187–193, Feb. 1993.

Karpeisky et al., Formation and properties of S–protein complex with S–peptide–containing fusion protein, FEBS Lett., 339:209–212, Feb. 1994.

Derman et al., Mutations that allow disulphide bond formation in the cytoplasm of *Escherichia coli*, Science, 262:1744–1747, Dec. 1993.

Morrissey et al., Molecular cloning of the cDNA for tissue factor, the cellular receptor for the initiation of the coagulation protease cascade, Cell, 50:129–135, Jul. 1987.

*Primary Examiner*—Lorraine Spector
*Assistant Examiner*—Claire M. Kaufman
*Attorney, Agent, or Firm*—Quarles & Brady

[57] ABSTRACT

Recombinant rabbit tissue factor is cloned and produced in a bacterial host. This protein, which is relatively insoluble and has several disulfide bonds, requires special modifications in order to express and be purified at commercial levels. By expressing the tissue factor as a fusion protein with a bacterial enzyme, thioredoxin, solubility is increased. Use of a thioredoxin reductase deficient host aids in proper tertiary structure for biological activity.

11 Claims, No Drawings

RECOMBINANT RABBIT TISSUE FACTOR

FIELD OF THE INVENTION

The present invention relates to clone mammalian genes in general and relates, in particular, to the cloning and expression in commercially significant quantities of recombinant rabbit tissue factor.

BACKGROUND OF THE INVENTION

Mammalian tissue factor is a plasma membrane glycoprotein that binds to blood coagulation factor VII or factor VIIIa. The binding activity of tissue factor is the initiating event in the cascade of enzymatic activities which lead to blood coagulation and clot formation in mammals. Tissue factor is found in many cell types that are not exposed directly to flowing blood and is particularly abundant in the brain, lung, and placenta. Injuries that disrupt the endothelium bring factor VII into contact with tissue factor to initiate the cascade that leads to blood clotting and clot formation.

Protein tissue factor is a valuable biological commodity in commerce today. The main use of tissue factor is as a constituent of the standard blood clotting test procedure performed on patients prior to surgery. The coagulation test most commonly used is initiated by the interaction of tissue factor in vitro to other blood coagulation factors such as factor VII. Such in vitro tests, in several forms, are marketed by several companies throughout the world. One category of such tests is referred to as the prothrombin time (PT) test in which a series of enzymatic tests in vitro under controlled conditions is used to diagnose disfunctions in the blood coagulation system of patients. Up until recently, in all commercially available PT tests the PT reagents included a relatively crude tissue factor protein extracted from natural sources, typically rabbits. Rabbit brain and rabbit lung mixtures were subjected to a series of isolation and purification steps, resulting in a dried extract of rabbit tissue factor used commercially in PT kits. While the use of rabbit tissue factor from natural sources was practical and reasonably well defined, there was occasional variation in the activity and yield of rabbit tissue factor from those preparations, both due to seasonable variability in the abundance of tissue factor in rabbits as well as lot-to-lot variability due to normal variation of biological systems. Such tissue factor extracts could also come on occasion, containing other coagulation factors in small amounts and a variety of other poorly characterized constituents.

Accordingly, significant effort was extended toward cloning and isolating tissue factor for use in the recombinant production of tissue factor as a protein. This led to the cloning of human tissue factor from a variety of cDNA segments as described in U.S. Pat. No. 5,110,730. The purification and preparation of prothrombin time reagents from such recombinant human tissue factor is described in published PCT application WO 93/07492. Products have been introduced now into commerce based on the production and purification of recombinant human tissue factor. The methods used to produce recombinant human tissue factor have not been fully elucidated in the literature.

The cDNA of rabbit brain tissue factor has also been isolated and sequenced. Andrews et al., Gene, 96:265–269 (1991); Pawashe et al., Thrombosis and Haemostasis 66:3:315–320 (1991).

Using current techniques of modern molecular biology or genetic engineering, it has now become commonplace to produce therapeutic proteins in prokaryotic hosts reproduced in fermenters or other vessels. However, experience has revealed that certain proteins are more amenable to production in this fashion than others. For example, proteins which have a relatively large number of cysteines, which form disulfide bridges with other cysteines in a protein molecule, are often found to be inefficiently produced in a biologically active form in a prokaryotic host. The reason is that the protein assembly and processing machinery of prokaryotes differ significantly from that present in eukaryotes. If improper disulfide bridges are formed between the cysteine molecules of a protein, it will not be biologically active. Accordingly, proteins with many disulfide bonds are often difficult to be produced in commercially significant quantities in prokaryotic systems and thus are sometimes produced in eukaryotic host systems. This is less desirable commercially since the culture and fermentation facilities for eukaryotic cell culture systems are currently much more expensive than those required for prokaryotic protein production hosts.

Another difficulty in producing therapeutic proteins in prokaryotic hosts arises with proteins which are particularly hydrophobic or have strong hydrophobic regions. This difficulty arises because of solubility problems in the protein produced with the host. Poorly soluble proteins can be difficult to recover in economic quantities when expressed in prokaryotic host expression systems.

Native rabbit tissue factor is, like the human tissue factor, a membrane-bound protein containing three domains. One domain is an extracellular domain of 217 to 222 amino acids. There is also a hydrophobic putative transmembrane domain of 23 amino acids and a cytoplasmic domain of 20 to 21 amino acids. Thus the protein produced by the cloned rabbit tissue factor gene has a large and quite hydrophobic domain. In addition, there are four conserved cysteine residues in all known tissue factor sequences and the proper formation of the cysteine disulfide bonds is required to have proper biological activity for the tissue factor protein.

Summary of the Invention

The present invention is summarized in that a fusion protein incorporating rabbit tissue factor has been found to be producible at significant quantities in prokaryotic hosts. The present method is thus directed to a method for producing recombinant rabbit tissue factor in a prokaryotic protein production system.

The protein produced is a fusion protein including a prokaryotic protein portion for solubility, a marker protein portion for purification and a truncated rabbit tissue factor ("RTF") protein including only the extracellular and transmembrane regions of the mature protein.

The present invention is further characterized in the use of thioredoxin reductase deficient mutant prokaryotic host cells to produce recombinant rabbit tissue factor, to permit proper folding of expressed protein.

Other objects, advantages, and features of the present invention will become apparent from the following specification.

Detailed Description of the Invention

Tissue factor is a difficult protein to produce recombinantly, and purify in commercial amounts, due to its insoluble character and its tendency to form disulfide bonds inhibitory of proper biological function. Recombinant rabbit tissue factor has been expressed here in commercial amounts by a combination of techniques. By expressing the tissue factor protein as a truncation including only the extracellular and transmembrane domains, omitting a fifth non-essential cysteine residue, and omitting the cytoplasmic domain, solubility is increased somewhat. By expressing the protein as a fusion protein with the thioredoxin protein from *E. coli*, solubility is increased further. By expressing the fusion protein in an *E. coli* host strain which is deficient in thioredoxin reductase, the reduction of disulfide bonds is minimized and the yield of biologically active forms of the protein is increased.

Once a suitable bacterial host has been engineered to produce recombinant rabbit tissue factor, it becomes necessary to ferment the host at optimized levels and to purify economically the produced protein. It has been determined that proper induction of protein expression, and control of host metabolism at that time, facilitates efficient production of protein. Inclusion of special marker protein sequences in the recombinant protein can be used to facilitate protein purification.

As will be described in greater detail below, the cDNA for rabbit tissue factor was cloned by PCR amplified cloning based on published sequence data. The production of significant levels of protein in a heterologous host from this gene proved a more difficult proposition. Many expression strategies and constructions were tried before success was achieved. To facilitate understanding of the unique expression problem experienced with this gene and this problem, several of the unsuccessful attempts will be described below. In order to be successful, the vector construction had to express at high level, produce a somewhat soluble protein that actuated the crude blood clotting assay quickly and produce a protein that could be efficiently purified. The unsuccessful and successful strategies are summarized in the following Table 1.

lent to a control with no rRTF insert, intermediate (Interm.) indicates a result two times faster than background, while fast indicates a time several fold faster than background. Soluble purified protein level was measured after purification by the His.Tag marker protein domain. For the relipidated clotting assay, the negative controls were 64 seconds while positive controls with tissue factor were 15 seconds in time.

For the tests described in Table 1, the crude clotting assay was performed by inducing expression of the gene construct when $O.D._{600}$ was between 0.5 and 1.0, centrifugation of the culture, and then resuspension of the pellet in sonication buffer (40 mM Tris.Hcl pH 7.5, 150 mM NaCl, 0.1% Triton X-100, 1 mM PMSF). The cells were then lysed by sonication in two bursts of 20 seconds. After centrifugation at 37,500×G for 25 minutes, the soluble supernatant was saved. The unpurified supernatant was used diluted 10 to 25 fold in the clotting assay.

The relipidated clotting assay was performed using purified and lipidated RTF, prepared as described in Example 2 below. Clotting assays were conducted also as described in Example 2.

All of the constructs include the His.Tag marker. this is a region of 6 histidine residues used as a purification marker. The "OmpT sig. seq." is a signal peptide sequence from *E. coli* which was intended to direct export of the fusion protein to the periplasmic space. The S.Tag is a 15 amino acid sequence of the S-peptide from RNAse A, which has a specific affinity for the S-protein, the S.Tag thus serving as another purification marker. Bgal refers to a fusion of the enzyme beta-galactosidase, intended to aid in solubility. The TrxA notation refers to the thioredoxin A enzyme from *E. coli*, also intended to facilitate solubility. The host BL21DE3

TABLE 1

| Clone/Strain Construct Strategy | Expression Level | % Soluble | Crude Clotting Assay | Soluble Protein Yield mg/l | Purity | Relipidated Clotting Assay |
|---|---|---|---|---|---|---|
| pREN86-111/BL21DE3 OmpT sig seq-rRTf trunc.-His.Tag | Low | 30–40% | fast | 0.1–0.2 | 10–20% | 16 sec |
| pREN111-61/BL21DE3 OmpT sig seq-His.Tag-S.Tag-rRTF trunc. | Medium | <10% | fast | 0.1–0.2 | 20–25% | — |
| pREN77-32/BL21DE3 S.Tag-rRTF trunc. | High | <10% | Bkgd | — | — | — |
| pREN78-36/BL21DE3 S.Tag-rRTF trunc-His.Tag | Medium | <10% | Bkgd | — | — | — |
| pREN84-D/BL21DE3 His.Tag-S.Tag-rRTF trunc.-Bgal | High | <10% | Interm. | — | — | — |
| pREN96-C/BL21DE3 His.Tag-S.Tag-rRTF trunc. | High | <10% | Bkgd | 20[1] | 90% | 69 sec[2] |
| pKWY2766-9/GI724 TrxA-rRTF trunc. | High | <10% | Interm. | — | — | — |
| pKWY2767-A/BL21DE3 TrxA-His.Tag-S.Tag-rRTF trunc. | High | <10% | Interm. | — | — | — |
| pREN92-c/AD494DE3 S.Tag-rRTF trunc. | High | <10% | Interm. | 1–2 | 60–70% | 37 sec |
| pREN93-H/AD494DE3 S.Tag-rRTF trunc.-His.Tag | Medium | <10% | Interm. | — | — | — |
| pREN105/AD494DE3 His.Tag-S.Tag-rRTF trunc. | High | <10% | Interm. | 0.3–0.4 | 20–25% | 54 sec |
| pKWY2768-1/AD494DE3 TrxA-His.Tag-S.Tag-rRTF trunc. | High | <10% | Fast | 2 | 80% | 13.9 sec |

In the above table, expression level was graded low if below 0.5 mg/l, intermediate if more than 0.5 mg/l and less than 5 mg/l and high if in excess of 5 mg/l. For the crude clotting assay, background (Bkgd) indicates a time equivalent is thioredoxin reductase competent *E. coli* host, while the *E. coli* host strain AD494DE3 possesses a thioredoxin reductase mutation trxB such that the strain is effectively thioredoxin reductase deficient.

The use of the thioredoxin reductase mutant host strain was particularly important. The cytoplasm of *E. coli* is a strongly reducing environment which thus disfavors the formation of disulfide bonds. In the instance of (recombinant RTF), this inhibition of disulfide bond formation inhibited yield of biologically active protein. The thioredoxin reductase mutant was important, as the above table indicates, in achieving useful yield of the biologically active form of the protein.

The conclusion of this effort was that the fusion protein TrxA-His.Tag.S.Tag-rRTF trunc. gave acceptable expression levels at reasonable purity of the biologically active form of the protein.

All of these constructs were initially constructed in what is known as a pET vector (Novagen). These vectors include a T7 promoter upstream of the site of insertion of the coding sequence. The T7 RNA polymerase is provided from a DE3 lambda phage lysogen incorporated into the host genome. In the DE3 lysogen, the T7 RNA polymerase is under the control of the lac UV promoter, an inducible promoter. The expression of the desired fusion protein could be thus initiated by inducing the lac UV promoter, which is conveniently done by adding IPTG to the host medium.

The vector produced by this general method can be inducibly expressed in a thioredoxin reductase deficient *E. coli* DE3 lysogen host strain. In general, standard *E. coli* fermentation procedures can be followed except that it has been found that the control of metabolic rate of the bacteria is helpful. This can be done by controlling dissolved oxygen (D.O.) in the fermenter. By holding D.O. down to 40%, then permitting the host to grow at 25° C. until an optical density of 1.0 is achieved, a useful bacterial density is achieved. Then temperature is reduced, to about 16° C., to slow metabolic activity. Then the expression of rRTF is induced with IPTG. After completion of expression the cells can be harvested and purification initiated.

The purification begins with breaking the cells in a French Press. After centrifugation, the supernatant is passed through a column containing a His-Bind resin from Novagen. The detergent CHAPS is advantageously used to resuspend the RTF protein after it is eluted from the column using an Imidazole gradient.

Using the fusion protein technique and the purification methods described here, significant quantities of purified recombinant rabbit tissue factor can be achieved in a commercially competitive manner. The rRTF thus produced, by the methods described here, has a purity of 90% to 100% as determined by SDS-PAGE estimation. The rRTF is readily purified to solutions of 50 to 200 µg/ml concentration in which in excess of 90% of the protein in the aqueous solution is the desired fusion proteins. The fusion protein has 408 amino acids with a molecular weight of 45,299.93 daltons. Yet, the fusion protein exhibits all the same biological characteristics of the native RTF protein. By cleaving and removing the trxA fusion from the rRTF portion of the fusion protein, it has been possible to test unfused protein. These tests have revealed that the fusion protein has biological activity identical to the unfused. In addition, the use of the His.Tag and S.Tag marker proteins allows for convenient purification of the fusion protein. Hence overall production of active recombinant biologically active molecule is facilitated.

EXAMPLES

Example 1

Cloning of Rabbit Tissue Factor (RTF)

Rabbit brain mRNA was isolated using the Straight A's mRNA Isolation System from Novagen, using the manufacturer's protocol. Briefly, a rabbit brain frozen at −70° C. was ground with mortar and pestle in the presence of liquid nitrogen. After evaporation of the liquid nitrogen, the ground tissue was incubated with lysis buffer and DTT, and then homogenized. The mRNA was then isolated from the homogenate using Magnetight Oligo (dT) Particles (Novagen) according to the manufacturer's recommendation.

To amplify the RTF sequence, RT-PCR was used. Specific primers were designed so as to amplify the segment of RTF encoding the mature N-terminus to the end of the transmembrane domain. The first strand cDNA synthesis was performed using the following RTF-specific antisense primer:

Primer name = 3'-TCJ-Stop

BglII    HindIII    XbaI

5'-GAAGATCTGCAAGCTTTCTAGACTAGTACACGGTCACAGACAGGACGA- 3'

This primer was designed based on the published rabbit tissue factor cDNA sequences from rabbit heart (Genebank accession number M55390) and rabbit brain (Genebank accession number X53521). The RTF specific bases in the primer above are underlined, and correspond to bases 720–698 in X53521 and bases 843–821 in M55390. This primer was designed to bind at the C-terminal end of the transmembrane coding region of the expressed RTF protein. A 10 µl first strand cDNA reaction was performed using MMLV-Reverse Transcriptase from New England Biolabs according to the manufacturer's instructions. 1.9 µg of poly A-mRNA was used as template in the reaction. The antisense primer 3'-TCJ-Stop was used at a final concentration of 1 pmol/µl to prime the first strand cDNA synthesis reaction.

The 10 µl first strand cDNA synthesis reaction was then used as a template in a 100 µl PCR reaction. The following RTF-specific sense primer was used in the second reaction.

Primer name = 5'-NTED-RTF

BamHI    MscI

5'-CGGGATCCACTGGCCATCGCAGACACTACAGGTAGAGCATA-3'

Again the RTF-specific bases are underlined. These bases correspond to bases 1–23 of X53521 and bases 124–146 of M55390. This primer is designed to bind to sequences encoding the N-terminal end of the mature protein, corresponding to the first amino acid after the signal sequence cleavage site. Thus this PCR reaction was intended to amplify the mature N-terminus of the extracellular domain to the transmembrane domain of RTF, but not the cytoplasmic domain.

The PCR reaction was performed with Taq polymerase using standard PCR conditions. The final concentration of both sense and antisense primers was 0.1 pmol/µl.

The PCR cycling was at 94° C. for 1 minute followed by 60° C. for 1 minute and 72° C. for 2 minutes, with this cycle repeated 35 times. The PCR primers also include the restriction enzyme sites in regions 5' to the rabbit tissue sequences as shown above, to facilitate later subcloning.

The PCR product was loaded into a 1.2% agarose gel and the desired 763 base pair band was cut from the gel and isolated using Prep-a-Gene matrix from Bio-Rad. The isolated RTF-PCR product was then cloned into the commercial plasmid pT7Blue(R) T-Vector (Novagen) according to the manufacturer's instructions. The recombinant plasmid was isolated by standard procedures.

The sequence of the subcloned RTF-PCR product and the primers used for amplification were verified by sequencing multiple recombinants. This was done with a Sequenase kit (USB) and flanking vector specific primers as well as RTF specific sequencing primers to verify the lack of PCR based mutations. The RTF region of clone pREN 70-A matched a composite of the sequences found in X53521 and M55390. This clone include nucleotides 1–18 from 5' NTED-RTF, followed by 719 nucleotides of RTF, followed by another 24 nucleotides from 3'-TCJ-STOP.

The RTF cDNA fragment was then subcloned from the pT7Blue(R) recombinant pREN 70-A as a BamHI and HindIII fragment into an E. coli expression vector pET32b (+) (Novagen), to create pKWY2768. This recombinant plasmid was isolated from the non-expression host NovaBlue and the cloning junctions verified by sequencing with flanking vector primers.

The SEQ ID NO: 3 below sets forth the nucleotide sequence of pKWY2768. SEQ ID NO: 1 sets forth the coding region for the fusion protein, the sequence of which is SEQ ID NO: 2. In that SEQ ID NO: 1, nucleotides 1–327 of E. coli thioredoxin A, nucleotides 349–366 encode the His.Tag marker, nucleotides 376–393 encode a thrombin cleavage site, nucleotides 400–444 encode the S.Tag marker protein (S-peptide), nucleotides 460–474 encode an enterokinase cleavage site, and nucleotides 505–1224 encode the truncated RTF open reading frame.

The plasmid pKWY2768 was transformed into the trxB (thioredoxin reductase null mutant), T7 RNA pol expression host AD494DE3, available from Novagen. The genotype of AD494DE3 includes Δ ara-leu 7967 Δ lac X74 Δpho AP vull pho R Δmal F3 F$^1$(lac+(LACL$^8$)pro) trx B::kan (DE3). The expression of this fusion protein was induced by the addition of IPTG as described in the pET Expression Manual from Novagen.

Example 2

Fermentation and Purification

Fermentation.

A glycerol stock of AD494(DE3) cells harboring the plasmid pKWY2768 was used to streak an LB plate containing 0.05 mg/ml carbenicillin and 0.015 mg/ml kanamycin. The culture was allowed to grow overnight at 37° C. A single colony from this plate was used to inoculate 50 ml of LB medium containing 0.05 mg/ml carbenicillin and 0.015 mg/ml kanamycin. The culture was incubated in a shaking incubator (275 RPM) at 37° C. until an O.D.$_{600}$ of approximately 1.5 was achieved. These cells were then used to inoculate two flasks containing 500 ml of LB media with carbenicillin and kanamycin at the same levels. These flasks were cultured overnight at 25° C. shaking at 275 RPM. An O.D.$_{600}$ of 1.5 was obtained.

These cells were then transferred to a Chemap fermenter (20 L total volume) and used as the inoculum for 15 liters of LB media containing 50 mg/L carbenicillin and 15 mg/L kanamycin. The dissolved oxygen was maintained at 40% throughout the fermentation. A temperature of 25° C. was maintained in the fermentation vessel until O.D.$_{600}$ reached 0.7, after which the temperature was reduced to 16° C. After the cells were equilibrated at 16° C., the RTF fusion protein was induced using 1 mM IPTG. The total time of induction was 3.5 hours. Following induction, the temperature was lowered to 4° C. for 2 hours. The cells were then harvested by centrifugation at 11,000×G for 8 minutes at 4° C., yielding approximately 50 grams of cell paste. The cell paste was stored frozen at −20° C.

Purification.

Frozen cell paste was resuspended by gently swirling in cold Novagen 1× Binding Buffer with CHAPS added (500 mM NaCl, 20 mM Tris-HCl ph 7.9, 5 mM Imidazole, 10 mM CHAPS). Buffer was added at a rate of 1.5 ml per gram of cell paste, while the cell paste was maintained on ice. The cells were then broken using the SimAminco French Press and a large pressure cell (50 ml volume). The cells were pressed three times at 4000 lbs. of pressure and one time at 10000 lbs. of pressure. Cell debris and most insoluble components were removed by centrifugation at 37,500×G for 25 minutes at 4° C. The supernatant was collected and loaded on a 30 ml settled bed charged His-Bind resin column (Novagen) prepared according to the manufacturer's directions and maintained at 4° C. The column was washed with ten column volumes of Novagen's 1× Wash Buffer with 10 mM CHAPS (500 mM NaCl, 20 mM Tris-Hcl pH 7.9, 60 mM Imidazole, 10 mM CHAPS) again at 4° C. The protein was eluted from the column using Novagen 1× Elution buffer using an Imidazole gradient from 60 mM to 500 mM. The 60 mM Imidazole Elution buffer contained 500 mM NaCl, 20 mM Tris-Hcl pH 7.9, 60 mM Imidazole, 10 mM CHAPS. The 500 mM Imidazole Elution buffer was identical except that Imidazole was at 500 mM. Fractions were collected (6 ml each) and assayed for the presence of protein. The fractions containing rRTF were pooled.

Lipidation and Clotting Assay

The buffer used in the purification step was then exchanged by dialysis against a buffer more favorable for proper lipidation. First the protein was diluted to 100 μg/ml in a dialysis buffer of 20 mM Tris-Hcl pH 8.0, 150 mM NaCl, 200 mM Mannitol and 20 mM CHAPS after which the diluted protein was dialyzed (10,000 to 12,000 mw cut-off membrane) for several hours at room temperature against the same buffer.

The standard lipidation procedure was that 48 μl of 100 μg/ml rRTF (100 mM final concentration), 50 μl lipids (14.7 mg/ml if needed: 5:32 Phosphatidyl Ethanolamine, phosphatidyl choline in 0.25% Deoxycholate), 1 μl 250 mM CdCl$_2$, and 899 μl HBS buffer pH 7.0, for a final volume of 1 ml. The mixture was incubated at 37° C. for 1 hour followed by dialysis overnight at room temperature in HBS buffer (140 mM NaCl, 10 mM HEPES, pH 7.0).

The clotting assay was performed by mixing 100 μl of the lipidated rRTF with 100 μl of 20 mM CaCl$_2$ in a fibrometer cup, incubating at 37° C. for 5 minutes, and adding 100 μl Citrol Level I plasma (Baxter) equilibrated at 37° C. At the same time the plasma is added, the fibrometer timer is started. The timer stops when a clot forms. The resultant time is prothrombin time or PT. For Factor VII deficient times, a Factor VII deficient plasma was used in substitution for the Citrol Level 1 plasma.

Results.

The rRTF protein produced exhibited a normal plasma clot time of 7.7 seconds and a Factor VII deficient clot time of 54.7 seconds. Thus the Factor VII deficient-to-normal ratio was 7.10. The rRTF purity was greater than 95%.

Example 3

This batch was fermented and purified as in Example 2 except that the O.D. at induction was 1.2 and the induction temperature was 18° C.

The normal plasma clot time of this batch was 8.9 seconds and the Factor VII deficient time was 42 seconds, for a deficient-to-active ration of 4.76. The purity was in excess of 90%.

Example 4

This batch was fermented and purified as in Example 2 above except that induction temperature was 20° C. and the time of induction was 3.0 hours.

The normal plasma clot time of this rRTF batch was 8.9 seconds and the Factor VII deficient time was 51.9 seconds for a ratio of 5.83. The purity was in excess of 95%.

Examples 5–10

These batches were performed as above except that the optical density at induction and induction temperature were varied. The results are tabulated in the following Table 2, along with the results from Examples 2–4 above.

TABLE 2

| O.D. at Induction | Induction Temp. | Soluble Purified Protein Yield | Relipidated Clotting Activity |
|---|---|---|---|
| 0.7 | 25° C. | Med | Med |
| 0.7 | 20 | Med | Med |
| 0.7 | 18 | Med | High |
| 0.7 | 16 | Med | High |
| 0.7 | 4 | Low | High |
| 1.0 | 25 | High | Med |
| 1.0 | 20 | Med | Med |
| 1.2 | 18 | High | High |
| 1.4 | 25 | High | Low |

| Soluble Purified rRTF Yield | Relipidated Clotting Activity (using PE:PS:PC lipid mixture) |
|---|---|
| High = >1 mg/L | High = <10 sec |
| Med = 0.5–1.0 mg/L | Med = 10–15 sec |
| Low = 0.0–0.5 mg/L | Low = >15 sec |

Example 11

Clot Time Studies

To evaluate the clotting characteristics of rRTF, rRTF prepare as described above was compared to recombinant human tissue factor, rHTF, which is available commercially. For these studies, both rHTF and rRTF were tested pre and post lipidation and with both normal and Factor VII deficient plasma. It is preferred in a commercial clotting test kit that the ratio of normal to Factor VII deficient times be high, in order to have the best consistency in results.

For these studies, lipidation was performed as described in Example 2 above. The rHTF was similarly lipidated. The lipidated tissue factor was diluted using HBS buffer and the coagulation assay performed for each dilution.

The clotting or coagulation assay was performed as described in Example 2.

The results obtained were summarized in the following Table 3.

TABLE 3

| | Pre-lipidation | | | Post-lipidation | | |
|---|---|---|---|---|---|---|
| | Normal | Factor VII def. | Ratio | Normal | Factor VII def. | Ratio |
| | | | rHTF (averages) | | | |
| 100 nM | 7.2 | 54.3 | 7.54 | 7.2 | 54.3 | 7.54 |
| 50 nM | 8.2 | 65.7 | 8.01 | 7.2 | 46.0 | 6.39 |
| 20 nM | 8.3 | 57.2 | 6.89 | 7.4 | 40.7 | 5.50 |
| 10 nM | 11.0 | 58.9 | 5.35 | 8.1 | 45.6 | 5.63 |
| 5 nM | 11.7 | 56.9 | 4.89 | 8.9 | 53.0 | 5.96 |
| | | | rRTF (averages) | | | |
| 100 nM | 7.7 | 54.7 | 7.10 | 7.7 | 54.7 | 7.10 |
| 50 nM | 8.8 | 67.7 | 7.69 | 7.6 | 55.1 | 7.25 |
| 20 nM | 10.6 | 64.9 | 6.12 | 8.5 | 48.5 | 5.71 |
| 10 nM | 11.9 | 66.7 | 5.60 | 9.0 | 55.0 | 6.4 |
| 5 nM | 15.5 | 74.6 | 4.81 | 9.8 | 72.3 | 7.36 |

Thus, the rRTF exhibited in this study an improved ratio compared to rHTF.

We claim:

1. A substantially purified preparation of a fusion protein, the fusion protein comprising, in order from amino terminus toward carboxy terminus:

the thioredoxin A protein from *E. coli*;

multiple contiguous histidine residues;

a S-peptide; and a truncated rabbit tissue factor sequence including the extracellular and transmembrane domains, and not the cytoplasmic domain of a native mature rabbit tissue factor protein, wherein the truncated tissue factor protein functions as a part of the blood coagulation cascade.

2. A preparation as claimed in claim 1 wherein the protein is suspended in an aqueous buffer containing CHAPS.

3. A method of making recombinant rabbit tissue factor comprising the steps of:

(a) culturing a thioredoxin reductase deficient bacterial host which harbors a fusion protein coding sequence including a thioredoxin A protein coding sequence, a sequence encoding multiple contiguous histidine residues; a S-peptide coding sequence, and a truncated rabbit tissue factor coding sequence including the extracellular and transmembrane domains but not the cytoplasmic domain of the native mature protein, the coding sequences all in a single open reading frame under the control of an inducible promoter, the culturing performed until a desired level of the host is achieved without inducing the promoter;

(b) cooling the bacterial host to slow its metabolic activity;

(c) inducing the promoter to initiate fusion protein expressing in the host;

(d) lysing the host cells; and (e) recovering the fusion protein from the lysed cells by passage through a column having a specific affinity for one of the multiple histidines or the S-peptide.

4. The method of claim 3 wherein the inducible promoter is the lac UV promoter and induction of the promoter is performed by addition of IPTG.

5. The method of claim 3 wherein the inducible promoter is a T7 promoter which is induced by a lac operator and wherein a lac UV promoter is placed in the host upstream of a DE3 lysogen coding sequence for T7 RNA polymerase so that induction of the lac UV promoter results in initiation of T7 RNA polymerase expression to activate expression of the fusion protein.

6. The method of claim 3 wherein the host cells are lysed by pressing in a French press.

7. A method of making soluble biologically active recombinant rabbit tissue factor comprising the steps of:

(a) constructing a gene construct encoding a fusion protein including a thioredoxin A protein coding sequence linked to the extracellular and transmembrane domains, but not the cytoplasmic domain, of rabbit tissue factor, the gene construct being under the control of an inducible promoter;

(b) placing the gene construct in a bacterial thioredoxin reductase deficient host strain deficient in thioredoxin reductase activity;

(c) culturing the bacterial host strain;

(d) inducing the promoter in the gene construct to express the fusion protein; and (e) recovering the fusion protein from the host cells.

8. The method of claim 7 wherein the gene construct includes sequences to express a marker protein as part of the fusion protein and wherein the recovering step (e) is performed by affinity purification of the marker protein.

9. The method of claim 8 wherein the marker protein is a sequence containing multiple contiguous histidine residues.

10. A product of manufacture comprising an aqueous solution containing a fusion protein constituting in excess of 90% purity of soluble protein in the solution, the fusion protein having a molecular weight in excess of 40 kDa and having the biological activity, as measured by clotting assay, of rabbit tissue factor, the fusion protein comprising, in order from amino terminus toward carboxy terminus, the thioredoxin A protein from *E. coli*; multiple successive histidine residues; a S-peptide; and a truncated rabbit tissue factor sequence including the extracellular and transmembrane domains, and not the cytoplasmic domain of the native mature protein.

11. A substantially purified preparation of a fusion protein, the fusion protein comprising, in order from amino terminus toward carboxy terminus;

the thioredoxin A protein from *E. coli*;

at least six contiguous histidine residues;

a S-peptide; and a truncated rabbit tissue factor sequence including the extracellular and transmembrane domains, and not the cytoplasmic domain of the native mature protein, the truncated tissue factor protein being capable of functioning as a part of the blood coagulation cascade;

wherein the fusion protein has the sequence of SEQ ID NO:2.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1227 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "Recombinant gene encoding trxA-rabbit tissue factor fusion protein"

( i x ) FEATURE:
    ( A ) NAME/KEY: CDS
    ( B ) LOCATION: 1..1227

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | AGC | GAT | AAA | ATT | ATT | CAC | CTG | ACT | GAC | GAC | AGT | TTT | GAC | ACG | GAT | 48 |
| Met | Ser | Asp | Lys | Ile | Ile | His | Leu | Thr | Asp | Asp | Ser | Phe | Asp | Thr | Asp | |
| 1 | | | | 5 | | | | | 10 | | | | | 15 | | |
| GTA | CTC | AAA | GCG | GAC | GGG | GCG | ATC | CTC | GTC | GAT | TTC | TGG | GCA | GAG | TGG | 96 |
| Val | Leu | Lys | Ala | Asp | Gly | Ala | Ile | Leu | Val | Asp | Phe | Trp | Ala | Glu | Trp | |
| | | | 20 | | | | | 25 | | | | | 30 | | | |
| TGC | GGT | CCG | TGC | AAA | ATG | ATC | GCC | CCG | ATT | CTG | GAT | GAA | ATC | GCT | GAC | 144 |
| Cys | Gly | Pro | Cys | Lys | Met | Ile | Ala | Pro | Ile | Leu | Asp | Glu | Ile | Ala | Asp | |
| | | 35 | | | | | 40 | | | | | 45 | | | | |
| GAA | TAT | CAG | GGC | AAA | CTG | ACC | GTT | GCA | AAA | CTG | AAC | ATC | GAT | CAA | AAC | 192 |
| Glu | Tyr | Gln | Gly | Lys | Leu | Thr | Val | Ala | Lys | Leu | Asn | Ile | Asp | Gln | Asn | |
| | 50 | | | | | 55 | | | | | 60 | | | | | |
| CCT | GGC | ACT | GCG | CCG | AAA | TAT | GGC | ATC | CGT | GGT | ATC | CCG | ACT | CTG | CTG | 240 |
| Pro | Gly | Thr | Ala | Pro | Lys | Tyr | Gly | Ile | Arg | Gly | Ile | Pro | Thr | Leu | Leu | |
| 65 | | | | | 70 | | | | | 75 | | | | | 80 | |
| CTG | TTC | AAA | AAC | GGT | GAA | GTG | GCG | GCA | ACC | AAA | GTG | GGT | GCA | CTG | TCT | 288 |
| Leu | Phe | Lys | Asn | Gly | Glu | Val | Ala | Ala | Thr | Lys | Val | Gly | Ala | Leu | Ser | |
| | | | | 85 | | | | | 90 | | | | | 95 | | |
| AAA | GGT | CAG | TTG | AAA | GAG | TTC | CTC | GAC | GCT | AAC | CTG | GCC | GGT | TCT | GGT | 336 |
| Lys | Gly | Gln | Leu | Lys | Glu | Phe | Leu | Asp | Ala | Asn | Leu | Ala | Gly | Ser | Gly | |
| | | | 100 | | | | | 105 | | | | | 110 | | | |
| TCT | GGC | CAT | ATG | CAC | CAT | CAT | CAT | CAT | CAT | TCT | TCT | GGT | CTG | GTG | CCA | 384 |
| Ser | Gly | His | Met | His | His | His | His | His | His | Ser | Ser | Gly | Leu | Val | Pro | |
| | | 115 | | | | | 120 | | | | | 125 | | | | |
| CGC | GGT | TCT | GGT | ATG | AAA | GAA | ACC | GCT | GCT | GCT | AAA | TTC | GAA | CGC | CAG | 432 |
| Arg | Gly | Ser | Gly | Met | Lys | Glu | Thr | Ala | Ala | Ala | Lys | Phe | Glu | Arg | Gln | |
| | 130 | | | | | 135 | | | | | 140 | | | | | |
| CAC | ATG | GAC | AGC | CCA | GAT | CTG | GGT | ACC | GAC | GAC | GAC | GAC | AAG | GCC | ATG | 480 |
| His | Met | Asp | Ser | Pro | Asp | Leu | Gly | Thr | Asp | Asp | Asp | Asp | Lys | Ala | Met | |
| 145 | | | | | 150 | | | | | 155 | | | | | 160 | |
| GCG | ATA | TCG | GAT | CCA | CTG | GCC | ATC | GCA | GAC | ACT | ACA | GGT | AGA | GCA | TAT | 528 |
| Ala | Ile | Ser | Asp | Pro | Leu | Ala | Ile | Ala | Asp | Thr | Thr | Gly | Arg | Ala | Tyr | |
| | | | | 165 | | | | | 170 | | | | | 175 | | |
| AAT | CTA | ACT | TGG | AAG | TCA | ACG | AAT | TTC | AAG | ACA | ATT | CTG | GAG | TGG | GAA | 576 |
| Asn | Leu | Thr | Trp | Lys | Ser | Thr | Asn | Phe | Lys | Thr | Ile | Leu | Glu | Trp | Glu | |
| | | | 180 | | | | | 185 | | | | | 190 | | | |
| CCC | AAA | TCC | ATC | GAT | CAT | GTC | TAC | ACA | GTT | CAG | ATA | AGC | ACT | AGG | CTA | 624 |
| Pro | Lys | Ser | Ile | Asp | His | Val | Tyr | Thr | Val | Gln | Ile | Ser | Thr | Arg | Leu | |
| | | 195 | | | | | 200 | | | | | 205 | | | | |
| GAA | AAC | TGG | AAG | AGC | AAA | TGT | TTC | TTA | ACC | GCG | GAG | ACG | GAG | TGC | GAC | 672 |
| Glu | Asn | Trp | Lys | Ser | Lys | Cys | Phe | Leu | Thr | Ala | Glu | Thr | Glu | Cys | Asp | |
| | 210 | | | | | 215 | | | | | 220 | | | | | |
| CTC | ACC | GAT | GAG | GTC | GTG | AAG | GAC | GTG | GGG | CAG | ACG | TAC | ATG | GCG | CGG | 720 |
| Leu | Thr | Asp | Glu | Val | Val | Lys | Asp | Val | Gly | Gln | Thr | Tyr | Met | Ala | Arg | |
| 225 | | | | | 230 | | | | | 235 | | | | | 240 | |
| GTC | CTC | TCC | TAC | CCG | GCA | AGG | AAC | GGA | AAC | ACC | ACG | GGG | TTC | CCC | GAG | 768 |
| Val | Leu | Ser | Tyr | Pro | Ala | Arg | Asn | Gly | Asn | Thr | Thr | Gly | Phe | Pro | Glu | |
| | | | | 245 | | | | | 250 | | | | | 255 | | |
| GAG | CCT | CCC | TTT | AGA | AAC | TCC | CCG | GAG | TTC | ACG | CCG | TAC | CTG | GAC | ACA | 816 |
| Glu | Pro | Pro | Phe | Arg | Asn | Ser | Pro | Glu | Phe | Thr | Pro | Tyr | Leu | Asp | Thr | |
| | | | 260 | | | | | 265 | | | | | 270 | | | |
| AAC | CTC | GGC | CAG | CCA | ACA | ATT | CAG | AGC | TTT | GAA | CAA | GTT | GGG | ACA | AAA | 864 |
| Asn | Leu | Gly | Gln | Pro | Thr | Ile | Gln | Ser | Phe | Glu | Gln | Val | Gly | Thr | Lys | |
| | | 275 | | | | | 280 | | | | | 285 | | | | |
| CTG | AAT | GTG | ACA | GTC | CAG | GAT | GCA | CGC | ACG | CTG | GTC | AGA | AGG | AAT | GGG | 912 |
| Leu | Asn | Val | Thr | Val | Gln | Asp | Ala | Arg | Thr | Leu | Val | Arg | Arg | Asn | Gly | |

|  |  |  |  |  |  |  |  |  |  |  |  |  |  |  |  |
|---|---|---|---|---|---|---|---|---|---|---|---|---|---|---|---|
|  | 290 |  |  |  | 295 |  |  |  |  | 300 |  |  |  |  |  |
| ACA | TTC | CTA | AGT | CTC | CGG | GCT | GTG | TTT | GGC | AAG | GAC | TTG | AAT | TAC | ACG | 960 |
| Thr | Phe | Leu | Ser | Leu | Arg | Ala | Val | Phe | Gly | Lys | Asp | Leu | Asn | Tyr | Thr |
| 305 |  |  |  |  | 310 |  |  |  |  | 315 |  |  |  |  | 320 |
| CTT | TAT | TAC | TGG | AGA | GCT | TCG | AGC | ACA | GGA | AAG | AAA | ACA | GCC | ACG | ACA | 1008 |
| Leu | Tyr | Tyr | Trp | Arg | Ala | Ser | Ser | Thr | Gly | Lys | Lys | Thr | Ala | Thr | Thr |
|  |  |  |  | 325 |  |  |  |  | 330 |  |  |  |  |  | 335 |
| AAC | ACT | AAT | GAG | TTT | TTG | ATC | GAC | GTG | GAT | AAA | GGA | GAA | AAC | TAC | TGT | 1056 |
| Asn | Thr | Asn | Glu | Phe | Leu | Ile | Asp | Val | Asp | Lys | Gly | Glu | Asn | Tyr | Cys |
|  |  |  | 340 |  |  |  |  | 345 |  |  |  |  |  | 350 |  |
| TTC | AGT | GTC | CAA | GCA | GTG | ATT | CCC | TCT | CGG | AAA | AGG | AAG | CAG | AGG | AGC | 1104 |
| Phe | Ser | Val | Gln | Ala | Val | Ile | Pro | Ser | Arg | Lys | Arg | Lys | Gln | Arg | Ser |
|  |  | 355 |  |  |  |  |  | 360 |  |  |  |  | 365 |  |  |
| CCC | GAG | AGC | CTC | ACT | GAG | TGC | ACC | AGC | CGC | GAG | CAG | GGC | AGG | GCC | AGG | 1152 |
| Pro | Glu | Ser | Leu | Thr | Glu | Cys | Thr | Ser | Arg | Glu | Gln | Gly | Arg | Ala | Arg |
|  | 370 |  |  |  |  |  | 375 |  |  |  |  | 380 |  |  |  |
| GAG | ATG | TTC | TTC | ATC | ATT | GGA | GCA | GTG | GTG | GTC | GTG | GCC | CTC | TTG | ATC | 1200 |
| Glu | Met | Phe | Phe | Ile | Ile | Gly | Ala | Val | Val | Val | Val | Ala | Leu | Leu | Ile |
| 385 |  |  |  |  | 390 |  |  |  |  | 395 |  |  |  |  | 400 |
| ATC | GTC | CTG | TCT | GTG | ACC | GTG | TAC | TAG |  |  |  |  |  |  |  | 1227 |
| Ile | Val | Leu | Ser | Val | Thr | Val | Tyr | * |
|  |  |  |  | 405 |

( 2 ) INFORMATION FOR SEQ ID NO:2:

( i ) SEQUENCE CHARACTERISTICS:
        ( A ) LENGTH: 408 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ser | Asp | Lys | Ile | Ile | His | Leu | Thr | Asp | Asp | Ser | Phe | Asp | Thr | Asp |
|---|---|---|---|---|---|---|---|---|---|---|---|---|---|---|---|
| 1 |  |  |  | 5 |  |  |  |  | 10 |  |  |  |  | 15 |  |
| Val | Leu | Lys | Ala | Asp | Gly | Ala | Ile | Leu | Val | Asp | Phe | Trp | Ala | Glu | Trp |
|  |  |  | 20 |  |  |  |  | 25 |  |  |  |  | 30 |  |  |
| Cys | Gly | Pro | Cys | Lys | Met | Ile | Ala | Pro | Ile | Leu | Asp | Glu | Ile | Ala | Asp |
|  |  | 35 |  |  |  |  | 40 |  |  |  |  | 45 |  |  |  |
| Glu | Tyr | Gln | Gly | Lys | Leu | Thr | Val | Ala | Lys | Leu | Asn | Ile | Asp | Gln | Asn |
|  | 50 |  |  |  |  | 55 |  |  |  |  | 60 |  |  |  |  |
| Pro | Gly | Thr | Ala | Pro | Lys | Tyr | Gly | Ile | Arg | Gly | Ile | Pro | Thr | Leu | Leu |
| 65 |  |  |  |  | 70 |  |  |  |  | 75 |  |  |  |  | 80 |
| Leu | Phe | Lys | Asn | Gly | Glu | Val | Ala | Ala | Thr | Lys | Val | Gly | Ala | Leu | Ser |
|  |  |  |  | 85 |  |  |  |  | 90 |  |  |  |  | 95 |  |
| Lys | Gly | Gln | Leu | Lys | Glu | Phe | Leu | Asp | Ala | Asn | Leu | Ala | Gly | Ser | Gly |
|  |  |  | 100 |  |  |  |  | 105 |  |  |  |  | 110 |  |  |
| Ser | Gly | His | Met | His | His | His | His | His | His | Ser | Ser | Gly | Leu | Val | Pro |
|  |  | 115 |  |  |  |  | 120 |  |  |  |  | 125 |  |  |  |
| Arg | Gly | Ser | Gly | Met | Lys | Glu | Thr | Ala | Ala | Ala | Lys | Phe | Glu | Arg | Gln |
|  | 130 |  |  |  |  | 135 |  |  |  |  | 140 |  |  |  |  |
| His | Met | Asp | Ser | Pro | Asp | Leu | Gly | Thr | Asp | Asp | Asp | Lys | Ala | Met |
| 145 |  |  |  |  | 150 |  |  |  |  | 155 |  |  |  |  | 160 |
| Ala | Ile | Ser | Asp | Pro | Leu | Ala | Ile | Ala | Asp | Thr | Thr | Gly | Arg | Ala | Tyr |
|  |  |  |  | 165 |  |  |  |  | 170 |  |  |  |  | 175 |  |
| Asn | Leu | Thr | Trp | Lys | Ser | Thr | Asn | Phe | Lys | Thr | Ile | Leu | Glu | Trp | Glu |
|  |  |  | 180 |  |  |  |  | 185 |  |  |  |  | 190 |  |  |
| Pro | Lys | Ser | Ile | Asp | His | Val | Tyr | Thr | Val | Gln | Ile | Ser | Thr | Arg | Leu |
|  |  | 195 |  |  |  |  | 200 |  |  |  |  | 205 |  |  |  |

| | | | | | | | | | | | | | | |
|---|---|---|---|---|---|---|---|---|---|---|---|---|---|---|
| Glu | Asn | Trp | Lys | Ser | Lys | Cys | Phe | Leu | Thr | Ala | Glu | Thr | Glu | Cys | Asp |
| | | 210 | | | | 215 | | | | 220 | | | | | |
| Leu | Thr | Asp | Glu | Val | Val | Lys | Asp | Val | Gly | Gln | Thr | Tyr | Met | Ala | Arg |
| 225 | | | | | 230 | | | | | 235 | | | | | 240 |
| Val | Leu | Ser | Tyr | Pro | Ala | Arg | Asn | Gly | Asn | Thr | Thr | Gly | Phe | Pro | Glu |
| | | | | 245 | | | | | 250 | | | | | 255 | |
| Glu | Pro | Pro | Phe | Arg | Asn | Ser | Pro | Glu | Phe | Thr | Pro | Tyr | Leu | Asp | Thr |
| | | | 260 | | | | | 265 | | | | | 270 | | |
| Asn | Leu | Gly | Gln | Pro | Thr | Ile | Gln | Ser | Phe | Glu | Gln | Val | Gly | Thr | Lys |
| | | 275 | | | | | 280 | | | | | 285 | | | |
| Leu | Asn | Val | Thr | Val | Gln | Asp | Ala | Arg | Thr | Leu | Val | Arg | Arg | Asn | Gly |
| | | 290 | | | | 295 | | | | | 300 | | | | |
| Thr | Phe | Leu | Ser | Leu | Arg | Ala | Val | Phe | Gly | Lys | Asp | Leu | Asn | Tyr | Thr |
| 305 | | | | | 310 | | | | | 315 | | | | | 320 |
| Leu | Tyr | Tyr | Trp | Arg | Ala | Ser | Ser | Thr | Gly | Lys | Lys | Thr | Ala | Thr | Thr |
| | | | | 325 | | | | | 330 | | | | | 335 | |
| Asn | Thr | Asn | Glu | Phe | Leu | Ile | Asp | Val | Asp | Lys | Gly | Glu | Asn | Tyr | Cys |
| | | | 340 | | | | | 345 | | | | | 350 | | |
| Phe | Ser | Val | Gln | Ala | Val | Ile | Pro | Ser | Arg | Lys | Arg | Lys | Gln | Arg | Ser |
| | | 355 | | | | | 360 | | | | | 365 | | | |
| Pro | Glu | Ser | Leu | Thr | Glu | Cys | Thr | Ser | Arg | Glu | Gln | Gly | Arg | Ala | Arg |
| | 370 | | | | | 375 | | | | | 380 | | | | |
| Glu | Met | Phe | Phe | Ile | Ile | Gly | Ala | Val | Val | Val | Val | Ala | Leu | Leu | Ile |
| 385 | | | | | 390 | | | | | 395 | | | | | 400 |
| Ile | Val | Leu | Ser | Val | Thr | Val | Tyr | | | | | | | | |
| | | | | 405 | | | | | | | | | | | |

( 2 ) INFORMATION FOR SEQ ID NO:3:

( i ) SEQUENCE CHARACTERISTICS:
        ( A ) LENGTH: 6619 base pairs
        ( B ) TYPE: nucleic acid
        ( C ) STRANDEDNESS: double
        ( D ) TOPOLOGY: circular ( i i ) MOLECULE TYPE: other nucleic acid
        ( A ) DESCRIPTION: /desc = "Plasmid containing
          recombinant rabbit tissue factor gene."

( v i i ) IMMEDIATE SOURCE:
        ( B ) CLONE: pKWY2768

( x i ) SEQUENCE DESCRIPTION: SEQ ID NO:3:

| | | | | | |
|---|---|---|---|---|---|
| ATCCGGATAT | AGTTCCTCCT | TTCAGCAAAA | AACCCCTCAA | GACCCGTTTA | GAGGCCCCAA | 60 |
| GGGGTTATGC | TAGTTATTGC | TCAGCGGTGG | CAGCAGCCAA | CTCAGCTTCC | TTTCGGGCTT | 120 |
| TGTTAGCAGC | CGGATCTCAG | TGGTGGTGGT | GGTGGTGCTC | GAGTGCGGCC | GCAAGCTTTC | 180 |
| TAGACTAGTA | CACGGTCACA | GACAGGACGA | TGATCAAGAG | GGCCACGACC | ACCACTGCTC | 240 |
| CAATGATGAA | GAACATCTCC | CTGGCCCTGC | CCTGCTCGCG | GCTGGTGCAC | TCAGTGAGGC | 300 |
| TCTCGGGGCT | CCTCTGCTTC | CTTTTCCGAG | AGGGAATCAC | TGCTTGGACA | CTGAAACAGT | 360 |
| AGTTTTCTCC | TTTATCCACG | TCGATCAAAA | ACTCATTAGT | GTTTGTCGTG | GCTGTTTTCT | 420 |
| TTCCTGTGCT | CGAAGCTCTC | CAGTAATAAA | GCGTGTAATT | CAAGTCCTTG | CCAAACACAG | 480 |
| CCCGGAGACT | TAGGAATGTC | CCATTCCTTC | TGACCAGCGT | GCGTGCATCC | TGGACTGTCA | 540 |
| CATTCAGTTT | TGTCCCAACT | TGTTCAAAGC | TCTGAATTGT | TGGCTGGCCG | AGGTTTGTGT | 600 |
| CCAGGTACGG | CGTGAACTCC | GGGGAGTTTC | TAAAGGGAGG | CTCCTCGGGG | AACCCCGTGG | 660 |

```
TGTTTCCGTT CCTTGCCGGG TAGGAGAGGA CCCGCGCCAT GTACGTCTGC CCCACGTCCT    720
TCACGACCTC ATCGGTGAGG TCGCACTCCG TCTCCGCGGT TAAGAAACAT TTGCTCTTCC    780
AGTTTTCTAG CCTAGTGCTT ATCTGAACTG TGTAGACATG ATCGATGGAT TTGGGTTCCC    840
ACTCCAGAAT TGTCTTGAAA TTCGTTGACT TCCAAGTTAG ATTATATGCT CTACCTGTAG    900
TGTCTGCGAT GGCCAGTGGA TCCGATATCG CCATGGCCTT GTCGTCGTCG TCGGTACCCA    960
GATCTGGGCT GTCCATGTGC TGGCGTTCGA ATTTAGCAGC AGCGGTTTCT TTCATACCAG   1020
AACCGCGTGG CACCAGACCA GAAGAATGAT GATGATGATG GTGCATATGG CCAGAACCAG   1080
AACCGGCCAG GTTAGCGTCG AGGAACTCTT TCAACTGACC TTTAGACAGT GCACCCACTT   1140
TGGTTGCCGC CACTTCACCG TTTTGAACA GCAGCAGAGT CGGGATACCA CGGATGCCAT   1200
ATTTCGGCGC AGTGCCAGGG TTTTGATCGA TGTTCAGTTT TGCAACGGTC AGTTTGCCCT   1260
GATATTCGTC AGCGATTTCA TCCAGAATCG GGGCGATCAT TTTGCACGGA CCGCACCACT   1320
CTGCCCAGAA ATCGACGAGG ATCGCCCCGT CCGCTTTGAG TACATCCGTG TCAAAACTGT   1380
CGTCAGTCAG GTGAATAATT TTATCGCTCA TATGTATATC TCCTTCTTAA AGTTAAACAA   1440
AATTATTTCT AGAGGGGAAT TGTTATCCGC TCACAATTCC CCTATAGTGA GTCGTATTAA   1500
TTTCGCGGGA TCGAGATCGA TCTCGATCCT CTACGCCGGA CGCATCGTGG CCGGCATCAC   1560
CGGCGCCACA GGTGCGGTTG CTGGCGCCTA TATCGCCGAC ATCACCGATG GGGAAGATCG   1620
GGCTCGCCAC TTCGGGCTCA TGAGCGCTTG TTTCGGCGTG GGTATGGTGG CAGGCCCCGT   1680
GGCCGGGGGA CTGTTGGGCG CCATCTCCTT GCATGCACCA TTCCTTGCGG CGGCGGTGCT   1740
CAACGGCCTC AACCTACTAC TGGGCTGCTT CCTAATGCAG GAGTCGCATA AGGGAGAGCG   1800
TCGAGATCCC GGACACCATC GAATGGCGCA AAACCTTTCG CGGTATGGCA TGATAGCGCC   1860
CGGAAGAGAG TCAATTCAGG GTGGTGAATG TGAAACCAGT AACGTTATAC GATGTCGCAG   1920
AGTATGCCGG TGTCTCTTAT CAGACCGTTT CCCGCGTGGT GAACCAGGCC AGCCACGTTT   1980
CTGCGAAAAC GCGGGAAAAA GTGGAAGCGG CGATGGCGGA GCTGAATTAC ATTCCCAACC   2040
GCGTGGCACA ACAACTGGCG GGCAAACAGT CGTTGCTGAT TGGCGTTGCC ACCTCCAGTC   2100
TGGCCCTGCA CGCGCCGTCG CAAATTGTCG CGGCGATTAA ATCTCGCGCC GATCAACTGG   2160
GTGCCAGCGT GGTGGTGTCG ATGGTAGAAC GAAGCGGCGT CGAAGCCTGT AAAGCGGCGG   2220
TGCACAATCT TCTCGCGCAA CGCGTCAGTG GGCTGATCAT TAACTATCCG CTGGATGACC   2280
AGGATGCCAT TGCTGTGGAA GCTGCCTGCA CTAATGTTCC GGCGTTATTT CTTGATGTCT   2340
CTGACCAGAC ACCCATCAAC AGTATTATTT TCTCCCATGA AGACGGTACG CGACTGGGCG   2400
TGGAGCATCT GGTCGCATTG GGTCACCAGC AAATCGCGCT GTTAGCGGGC CCATTAAGTT   2460
CTGTCTCGGC GCGTCTGCGT CTGGCTGGCT GGCATAAATA TCTCACTCGC AATCAAATTC   2520
AGCCGATAGC GGAACGGGAA GGCGACTGGA GTGCCATGTC CGGTTTTCAA CAAACCATGC   2580
AAATGCTGAA TGAGGGCATC GTTCCCACTG CGATGCTGGT TGCCAACGAT CAGATGGCGC   2640
TGGGCGCAAT GCGCGCCATT ACCGAGTCCG GCTGCGCGT TGGTGCGGAC ATCTCGGTAG   2700
TGGGATACGA CGATACCGAA GACAGCTCAT GTTATATCCC GCCGTTAACC ACCATCAAAC   2760
AGGATTTTCG CCTGCTGGGG CAAACCAGCG TGGACCGCTT GCTGCAACTC TCTCAGGGCC   2820
AGGCGGTGAA GGGCAATCAG CTGTTGCCCG TCTCACTGGT GAAAAGAAAA ACCACCCTGG   2880
CGCCCAATAC GCAAACCGCC TCTCCCCGCG CGTTGGCCGA TTCATTAATG CAGCTGGCAC   2940
GACAGGTTTC CCGACTGGAA AGCGGGCAGT GAGCGCAACG CAATTAATGT AAGTTAGCTC   3000
ACTCATTAGG CACCGGGATC TCGACCGATG CCCTTGAGAG CCTTCAACCC AGTCAGCTCC   3060
```

-continued

| | | | | | |
|---|---|---|---|---|---|
| TTCCGGTGGG | CGCGGGGCAT | GACTATCGTC | GCCGCACTTA | TGACTGTCTT | CTTTATCATG | 3120 |
| CAACTCGTAG | GACAGGTGCC | GGCAGCGCTC | TGGGTCATTT | TCGGCGAGGA | CCGCTTTCGC | 3180 |
| TGGAGCGCGA | CGATGATCGG | CCTGTCGCTT | GCGGTATTCG | GAATCTTGCA | CGCCCTCGCT | 3240 |
| CAAGCCTTCG | TCACTGGTCC | CGCCACCAAA | CGTTTCGGCG | AGAAGCAGGC | CATTATCGCC | 3300 |
| GGCATGGCGG | CCCCACGGGT | GCGCATGATC | GTGCTCCTGT | CGTTGAGGAC | CCGGCTAGGC | 3360 |
| TGGCGGGGTT | GCCTTACTGG | TTAGCAGAAT | GAATCACCGA | TACGCGAGCG | AACGTGAAGC | 3420 |
| GACTGCTGCT | GCAAAACGTC | TGCGACCTGA | GCAACAACAT | GAATGGTCTT | CGGTTTCCGT | 3480 |
| GTTTCGTAAA | GTCTGGAAAC | GCGGAAGTCA | GCGCCCTGCA | CCATTATGTT | CCGGATCTGC | 3540 |
| ATCGCAGGAT | GCTGCTGGCT | ACCCTGTGGA | ACACCTACAT | CTGTATTAAC | GAAGCGCTGG | 3600 |
| CATTGACCCT | GAGTGATTTT | TCTCTGGTCC | CGCCGCATCC | ATACCGCCAG | TTGTTTACCC | 3660 |
| TCACAACGTT | CCAGTAACCG | GGCATGTTCA | TCATCAGTAA | CCCGTATCGT | GAGCATCCTC | 3720 |
| TCTCGTTTCA | TCGGTATCAT | TACCCCCATG | AACAGAAATC | CCCCTTACAC | GGAGGCATCA | 3780 |
| GTGACCAAAC | AGGAAAAAAC | CGCCCTTAAC | ATGGCCCGCT | TTATCAGAAG | CCAGACATTA | 3840 |
| ACGCTTCTGG | AGAAACTCAA | CGAGCTGGAC | GCGGATGAAC | AGGCAGACAT | CTGTGAATCG | 3900 |
| CTTCACGACC | ACGCTGATGA | GCTTTACCGC | AGCTGCCTCG | CGCGTTTCGG | TGATGACGGT | 3960 |
| GAAAACCTCT | GACACATGCA | GCTCCCGGAG | ACGGTCACAG | CTTGTCTGTA | AGCGGATGCC | 4020 |
| GGGAGCAGAC | AAGCCCGTCA | GGGCGCGTCA | GCGGGTGTTG | GCGGGTGTCG | GGGCGCAGCC | 4080 |
| ATGACCCAGT | CACGTAGCGA | TAGCGGAGTG | TATACTGGCT | TAACTATGCG | GCATCAGAGC | 4140 |
| AGATTGTACT | GAGAGTGCAC | CATATATGCG | GTGTGAAATA | CCGCACAGAT | GCGTAAGGAG | 4200 |
| AAAATACCGC | ATCAGGCGCT | CTTCCGCTTC | CTCGCTCACT | GACTCGCTGC | GCTCGGTCGT | 4260 |
| TCGGCTGCGG | CGAGCGGTAT | CAGCTCACTC | AAAGGCGGTA | ATACGGTTAT | CCACAGAATC | 4320 |
| AGGGGATAAC | GCAGGAAAGA | ACATGTGAGC | AAAAGGCCAG | CAAAAGGCCA | GGAACCGTAA | 4380 |
| AAAGGCCGCG | TTGCTGGCGT | TTTTCCATAG | GCTCCGCCCC | CCTGACGAGC | ATCACAAAAA | 4440 |
| TCGACGCTCA | AGTCAGAGGT | GGCGAAACCC | GACAGGACTA | TAAAGATACC | AGGCGTTTCC | 4500 |
| CCCTGGAAGC | TCCCTCGTGC | GCTCTCCTGT | TCCGACCCTG | CCGCTTACCG | GATACCTGTC | 4560 |
| CGCCTTTCTC | CCTTCGGGAA | GCGTGGCGCT | TTCTCATAGC | TCACGCTGTA | GGTATCTCAG | 4620 |
| TTCGGTGTAG | GTCGTTCGCT | CCAAGCTGGG | CTGTGTGCAC | GAACCCCCCG | TTCAGCCCGA | 4680 |
| CCGCTGCGCC | TTATCCGGTA | ACTATCGTCT | TGAGTCCAAC | CCGGTAAGAC | ACGACTTATC | 4740 |
| GCCACTGGCA | GCAGCCACTG | GTAACAGGAT | TAGCAGAGCG | AGGTATGTAG | GCGGTGCTAC | 4800 |
| AGAGTTCTTG | AAGTGGTGGC | CTAACTACGG | CTACACTAGA | AGGACAGTAT | TTGGTATCTG | 4860 |
| CGCTCTGCTG | AAGCCAGTTA | CCTTCGGAAA | AAGAGTTGGT | AGCTCTTGAT | CCGGCAAACA | 4920 |
| AACCACCGCT | GGTAGCGGTG | GTTTTTTTGT | TTGCAAGCAG | CAGATTACGC | GCAGAAAAAA | 4980 |
| AGGATCTCAA | GAAGATCCTT | TGATCTTTTC | TACGGGGTCT | GACGCTCAGT | GGAACGAAAA | 5040 |
| CTCACGTTAA | GGGATTTTGG | TCATGAGATT | ATCAAAAGG | ATCTTCACCT | AGATCCTTTT | 5100 |
| AAATTAAAAA | TGAAGTTTTA | AATCAATCTA | AAGTATATAT | GAGTAAACTT | GGTCTGACAG | 5160 |
| TTACCAATGC | TTAATCAGTG | AGGCACCTAT | CTCAGCGATC | TGTCTATTTC | GTTCATCCAT | 5220 |
| AGTTGCCTGA | CTCCCCGTCG | TGTAGATAAC | TACGATACGG | GAGGGCTTAC | CATCTGGCCC | 5280 |
| CAGTGCTGCA | ATGATACCGC | GAGACCCACG | CTCACCGGCT | CCAGATTTAT | CAGCAATAAA | 5340 |
| CCAGCCAGCC | GGAAGGGCCG | AGCGCAGAAG | TGGTCCTGCA | ACTTTATCCG | CCTCCATCCA | 5400 |
| GTCTATTAAT | TGTTGCCGGG | AAGCTAGAGT | AAGTAGTTCG | CCAGTTAATA | GTTTGCGCAA | 5460 |

-continued

| | | | | | | |
|---|---|---|---|---|---|---|
| CGTTGTTGCC | ATTGCTGCAG | GCATCGTGGT | GTCACGCTCG | TCGTTTGGTA | TGGCTTCATT | 5520 |
| CAGCTCCGGT | TCCCAACGAT | CAAGGCGAGT | TACATGATCC | CCCATGTTGT | GCAAAAAAGC | 5580 |
| GGTTAGCTCC | TTCGGTCCTC | CGATCGTTGT | CAGAAGTAAG | TTGGCCGCAG | TGTTATCACT | 5640 |
| CATGGTTATG | GCAGCACTGC | ATAATTCTCT | TACTGTCATG | CCATCCGTAA | GATGCTTTTC | 5700 |
| TGTGACTGGT | GAGTACTCAA | CCAAGTCATT | CTGAGAATAG | TGTATGCGGC | GACCGAGTTG | 5760 |
| CTCTTGCCCG | GCGTCAATAC | GGGATAATAC | CGCGCCACAT | AGCAGAACTT | TAAAAGTGCT | 5820 |
| CATCATTGGA | AAACGTTCTT | CGGGGCGAAA | ACTCTCAAGG | ATCTTACCGC | TGTTGAGATC | 5880 |
| CAGTTCGATG | TAACCCACTC | GTGCACCCAA | CTGATCTTCA | GCATCTTTTA | CTTTCACCAG | 5940 |
| CGTTTCTGGG | TGAGCAAAAA | CAGGAAGGCA | AAATGCCGCA | AAAAAGGGAA | TAAGGGCGAC | 6000 |
| ACGGAAATGT | TGAATACTCA | TACTCTTCCT | TTTTCAATAT | TATTGAAGCA | TTTATCAGGG | 6060 |
| TTATTGTCTC | ATGAGCGGAT | ACATATTTGA | ATGTATTTAG | AAAAATAAAC | AAATAGGGGT | 6120 |
| TCCGCGCACA | TTTCCCCGAA | AAGTGCCACC | TGAAATTGTA | AACGTTAATA | TTTTGTTAAA | 6180 |
| ATTCGCGTTA | AATTTTTGTT | AAATCAGCTC | ATTTTTTAAC | CAATAGGCCG | AAATCGGCAA | 6240 |
| AATCCCTTAT | AAATCAAAAG | AATAGACCGA | GATAGGGTTG | AGTGTTGTTC | CAGTTTGGAA | 6300 |
| CAAGAGTCCA | CTATTAAAGA | ACGTGGACTC | CAACGTCAAA | GGGCGAAAAA | CCGTCTATCA | 6360 |
| GGGCGATGGC | CCACTACGTG | AACCATCACC | CTAATCAAGT | TTTTTGGGGT | CGAGGTGCCG | 6420 |
| TAAAGCACTA | AATCGGAACC | CTAAAGGGAG | CCCCCGATTT | AGAGCTTGAC | GGGGAAAGCC | 6480 |
| GGCGAACGTG | GCGAGAAAGG | AAGGGAAGAA | AGCGAAAGGA | GCGGGCGCTA | GGGCGCTGGC | 6540 |
| AAGTGTAGCG | GTCACGCTGC | GCGTAACCAC | CACACCCGCC | GCGCTTAATG | CGCCGCTACA | 6600 |
| GGGCGCGTCC | CATTCGCCA | | | | | 6619 |

(2) INFORMATION FOR SEQ ID NO:4:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer 3'-TCJ-Stop"

(xi) SEQUENCE DESCRIPTION: SEQ ID NO:4:

| | | | | | |
|---|---|---|---|---|---|
| GAAGATCTGC | AAGCTTTCTA | GACTAGTACA | CGGTCACAGA | CAGGACGA | 48 |

(2) INFORMATION FOR SEQ ID NO:5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer 5'-NTED-RTF"

(xi) SEQUENCE DESCRIPTION: SEQ ID NO:5:

| | | | | |
|---|---|---|---|---|
| CGGGATCCAC | TGGCCATCGC | AGACACTACA | GGTAGAGCAT | A      41 |